(12) United States Patent
Maeda et al.

(10) Patent No.: US 7,939,241 B2
(45) Date of Patent: May 10, 2011

(54) (METH)ACRYLAMIDE DERIVATIVE, POLYMER, CHEMICALLY AMPLIFIED PHOTOSENSITIVE RESIN COMPOSITION, AND PATTERNING METHOD

(75) Inventors: Katsumi Maeda, Tokyo (JP); Kaichirou Nakano, Tokyo (JP)

(73) Assignee: NEC Corporation, Tokyo (JP)

( * ) Notice: Subject to any disclaimer, the term of this patent is extended or adjusted under 35 U.S.C. 154(b) by 606 days.

(21) Appl. No.: 11/919,891

(22) PCT Filed: May 12, 2006

(86) PCT No.: PCT/JP2006/309540
§ 371 (c)(1),
(2), (4) Date: Nov. 5, 2007

(87) PCT Pub. No.: WO2006/121150
PCT Pub. Date: Nov. 16, 2006

(65) Prior Publication Data
US 2009/0068587 A1    Mar. 12, 2009

(30) Foreign Application Priority Data
May 13, 2005 (JP) .................. 2005-141070

(51) Int. Cl.
G03F 7/039 (2006.01)
G03F 7/20 (2006.01)
G03F 7/30 (2006.01)
G03F 7/38 (2006.01)
G03F 7/40 (2006.01)

(52) U.S. Cl. ............ 430/270.1; 430/311; 430/326; 430/327; 430/328; 430/330; 430/905; 430/906; 430/910; 430/914; 526/304; 526/305; 526/307.7; 564/207

(58) Field of Classification Search ............ None
See application file for complete search history.

(56) References Cited

U.S. PATENT DOCUMENTS

| | | | |
|---|---|---|---|
| 4,339,521 A | | 7/1982 | Ahne et al. |
| 4,395,482 A | | 7/1983 | Ahne et al. |
| 5,326,840 A | * | 7/1994 | Przybilla et al. ............ 526/262 |
| 2002/0058201 A1 | | 5/2002 | Miyaji et al. |
| 2004/0265743 A1 | | 12/2004 | Lee et al. |

FOREIGN PATENT DOCUMENTS

| | | |
|---|---|---|
| EP | 1 101 774 A1 | 5/2001 |
| JP | 1-46862 | 10/1989 |
| JP | 3-36861 | 6/1991 |
| JP | 6-250448 A | 9/1994 |
| JP | 2001-172315 | 6/2001 |
| JP | 2004-40649 | 2/2002 |
| JP | 2002-162746 | 6/2002 |
| JP | 2003-241380 | 8/2003 |
| JP | 2004-219667 A | 8/2004 |
| JP | 2004-279662 A | 10/2004 |
| JP | 2005-15763 | 1/2005 |

OTHER PUBLICATIONS

Ueda et al., "New Convenient Synthetic Route for Photosensitive Poly(benzoxazole)," J. of Photopolymer Sci. & Tech., vol. 16, No. 2, pp. 237-242 (2003).
Ebara et al., "Chemically Amplified Photosensitive Poly(benzoxazole)," J. of Photopolymer Sci. & Tech., vol. 16, No. 2, pp. 287-292 (2003).

* cited by examiner

*Primary Examiner* — Sin J. Lee
(74) *Attorney, Agent, or Firm* — Young & Thompson

(57) ABSTRACT

The present invention relates to a novel (meth)acrylamide compound represented by the general formula (1), a (co) polymer of the (meth)acrylamide compound, and a chemically amplified photosensitive resin composition composed of the polymer and a photoacid generator. In the formula, $R^1$ represents a hydrogen atom or a methyl group; $R^2$ represents an acid-decomposable group; and $R^3$ to $R^6$ independently represent a hydrogen atom, a halogen atom or an alkyl group having 1 to 4 carbon atoms.

(1)

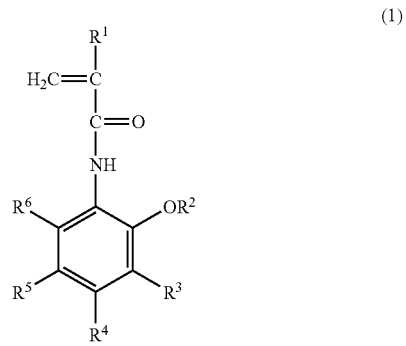

18 Claims, No Drawings

(METH)ACRYLAMIDE DERIVATIVE, POLYMER, CHEMICALLY AMPLIFIED PHOTOSENSITIVE RESIN COMPOSITION, AND PATTERNING METHOD

TECHNICAL FIELD

The present invention relates to a novel (meth)acrylamide derivative, a polymer, a chemically amplified photosensitive resin composition, and a patterning method. In particular, the present invention relates to a (meth)acrylamide derivative, a polymer, a chemically amplified photosensitive resin composition, and a patterning method being applicable to an interlayer insulating film and a surface protection film or the like of a semiconductor device.

BACKGROUND ART

Polyimide resins having excellent film properties such as heat resistance, mechanical properties and electric properties have been conventionally used for an interlayer insulating film or surface protection film of a semiconductor device. However, when a non-photosensitive polyimide resin is used as an interlayer insulating film or the like, a patterning process uses a positive resist, which requires etching and resist removal processes or the like, resulting in a more complex manufacturing process. The use of a photosensitive polyimide resin exhibiting excellent photo-sensitivity has investigated accordingly. Examples of such a photosensitive polyimide resin composition include positive photosensitive resin compositions consisting of a polyimidic acid, an aromatic bisazide compound and an amine compound described in Japanese Patent Publication No. 3-36861 (Patent Document 1). However, a development step in a patterning process of a photosensitive polyimide resin requires an organic solvent such as N-methyl-2-pyrrolidone and ethanol, which is problematic in terms of safety and environmental impact.

Thus, a positive photosensitive resin composition has recently been developed as a patterning material which can be developed with an aqueous alkaline solution such as an aqueous tetramethylammonium hydroxide (TMAH) solution used in a fine patterning process for a semiconductor. For example, Japanese Patent Publication No. 1-46862 (Patent Document 2) has described a non-chemical amplified positive photosensitive resin composition consisting of a polybenzoxazole precursor and a diazoquinone compound as a photosensitizing agent. M. Ueda et al., Journal of Photopolymer Science and Technology, Vol. 16(2), pp. 237 to 242 (2003) (Non-Patent Document 1) reported a non-chemical amplified positive photosensitive resin composition consisting of a polybenzoxazole precursor and a 1,2-naphthoquinonediazide-5-sulfonate. In addition, K. Ebara et al., Journal of Photopolymer Science and Technology, Vol. 16(2), pp. 287 to 292 (2003) (Non-Patent Document 2) reported a chemically amplified positive photosensitive resin composition consisting of a polybenzoxazole precursor protected by an acid-decomposable group and a photoacid generator.

In such a photosensitive resin composition, its structure is changed by heating to form a benzoxazole ring, resulting in excellent heat resistance and electric properties. For example, a polybenzoxazole precursor described in M. Ueda et al., Journal of Photopolymer Science and Technology, Vol. 16(2), pp. 237 to 242 (2003) (Non-Patent Document 1) forms a benzoxazole ring by heating after development with an alkaline solution as shown in the following reaction schemes A1 and A2. Since the benzoxazole ring is a stable structure, an interlayer insulating film or surface protection film prepared using a photosensitive composition consisting of the polybenzoxazole precursor exhibits excellent film properties such as heat resistance, mechanical properties and electric properties.

REACTION SCHEME A1

[Formula 1]

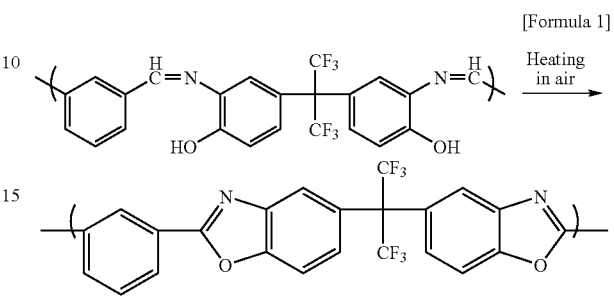

REACTION SCHEME A2

[Formula 2]

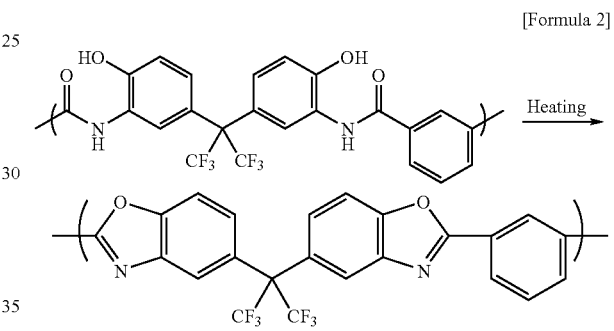

In the field of manufacturing a semiconductor device recently, a higher density, higher integration and a finer wiring pattern in the device have been further needed. Consequently, requirements have been stricter to a photosensitive resin composition used for an interlayer insulating film, surface protection film or the like. However, in view of resolution, any positive photosensitive resin composition described in the above Documents is not satisfactory.

It is therefore needed to develop photosensitive resin compositions which can be developed with an alkaline solution and exhibit higher resolution while maintaining the conventional film properties.

Patent Document 1: Japanese Patent Publication 3-36861
Patent Document 2: Japanese Patent Publication 146862
Non-Patent Document 1: M. Ueda et al., Journal of Photopolymer Science and Technology, Vol. 16(2), pp. 237 to 242 (2003)
Non-Patent Document 2: K. Ebara et al., Journal of Photopolymer Science and Technology, Vol. 16(2), pp. 287 to 292 (2003)

DISCLOSURE OF THE INVENTION

Problems to be solved by the Invention

Thus, a first object of the present invention for solving the above problems is to provide a (meth)acrylamide derivative and a polymer which can be preferably used as a raw material for a photosensitive resin composition. A second object is to provide a chemically amplified photosensitive resin composition exhibiting excellent film properties such as heat resistance, mechanical properties and electric properties, which can be developed with an alkaline solution and exhibit higher resolution. A third object is to provide a patterning method using a chemically amplified photosensitive resin composition.

Means to Solve the Problems

After intense investigation for achieving the above objects, the present inventors have found that a polymer prepared by polymerizing a monomer composition containing a novel (meth)acrylamide derivative having a particular structure is an excellent chemically amplified photosensitive resin composition which can be developed with an aqueous alkaline solution with higher resolution, and have thus achieved the present invention.

That is, the present invention provides a (meth)acrylamide derivative represented by the following general formula (1):

[Formula 3]

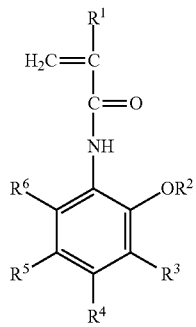

(1)

wherein $R^1$ represents a hydrogen atom or a methyl group;

$R^2$ represents an acid-decomposable group; and $R^3$ to $R^6$ independently represent a hydrogen atom, a halogen atom or an alkyl group having 1 to 4 carbon atoms.

The present invention provides a polymer comprising at least one repeating constitutional unit represented by the following general formula (2):

[Formula 4]

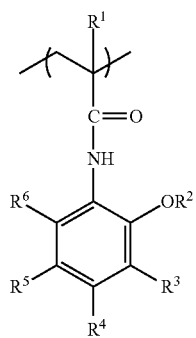

(2)

wherein $R^1$ represents a hydrogen atom or a methyl group;

$R^2$ represents an acid-decomposable group; and $R^3$ to $R^6$ independently represent a hydrogen atom, a halogen atom or an alkyl group having 1 to 4 carbon atoms.

The polymer is prepared by polymerizing a (meth)acrylamide derivative represented by the general formula (1) with a vinyl monomer copolymerizable with the (meth)acrylamide derivative.

Furthermore, the present invention provides the above polymer characterized by further comprising a constitutional unit represented by the following general formula (3) and/or a constitutional unit represented by the following general formula (4):

[Formula 5]

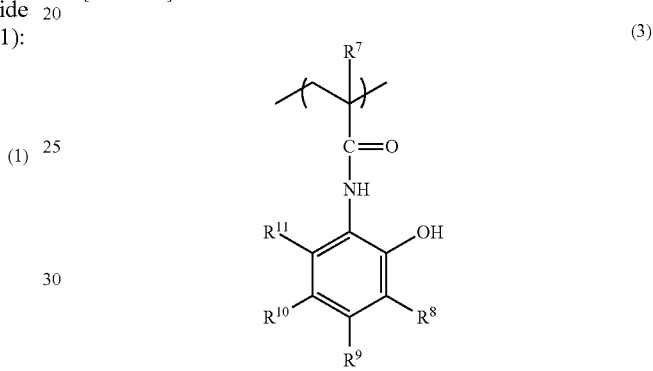

(3)

wherein $R^7$ represents a hydrogen atom or a methyl group; and $R^8$ to $R^{11}$ independently represent a hydrogen atom, a halogen atom or an alkyl group having 1 to 4 carbon atoms;

[Formula 6]

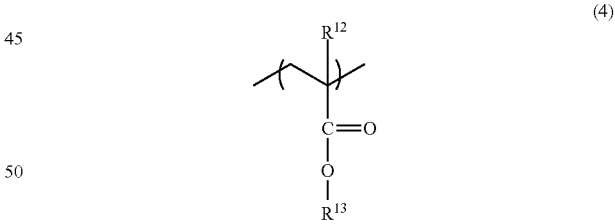

(4)

wherein $R^{12}$ represents a hydrogen atom or a methyl group; and $R^{13}$ represents an organic group having a lactone ring.

Preferably, the above polymer has a weight average molecular weight of 2,000 to 200,000.

The present invention provides a chemically amplified photosensitive resin composition comprising at least a polymer and a photoacid generator, the polymer containing at least one repeating constitutional unit selected from the group consisting of a repeating constitutional unit represented by the general formula (2) and a repeating constitutional unit represented by the general formula (3):

[Formula 7]

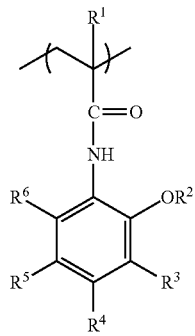

(2)

wherein $R^1$ represents a hydrogen atom or a methyl group;

$R^2$ represents an acid-decomposable group; and $R^3$ to $R^6$ independently represent a hydrogen atom, a halogen atom or an alkyl group having 1 to 4 carbon atoms,

[Formula 8]

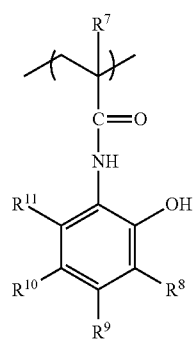

(3)

wherein $R^7$ represents a hydrogen atom or a methyl group; and $R^8$ to $R^{11}$ independently represent a hydrogen atom, a halogen atom or an alkyl group having 1 to 4 carbon atoms.

Preferably, the polymer containing at least one repeating constitutional unit selected from the group consisting of the repeating constitutional unit represented by the general formula (2) and the repeating constitutional unit represented by the general formula (3) is a polymer containing at least one repeating constitutional unit represented by the general formula (2).

Furthermore, the present invention provides the above chemically amplified photosensitive resin composition further comprising a dissolution inhibitor and/or an adhesion improver.

The dissolution inhibitor is characterized by being a compound represented by the following general formula (5) or the following general formula (6),

[Formula 9]

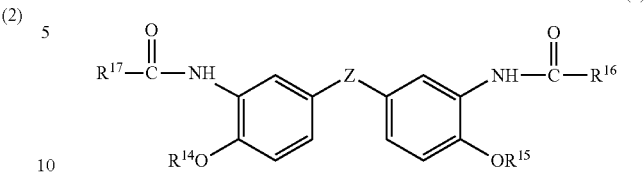

(5)

wherein $R^{14}$ and $R^{15}$ represent an acid-decomposable group;

$R^{16}$ and $R^{17}$ are a linear, branched or cyclic alkyl group or an aromatic hydrocarbon group having 1 to 10 carbon atoms; and Z represents a direct bond, —C(CF$_3$)$_2$—, —SO$_2$—, —CO—, —O—, or a divalent hydrocarbon group;

[Formula 10]

(6)

$$R^{22}\underset{OR^{19}}{\overset{}{\bigcirc}}\text{—NH—}\underset{O}{\overset{\|}{C}}\text{—R}^{18}\text{—}\underset{O}{\overset{\|}{C}}\text{—NH—}\underset{OR^{20}}{\overset{}{\bigcirc}}R^{21}$$

wherein $R^{18}$ represents a divalent hydrocarbon group;

$R^{19}$ and $R^{20}$ represent an acid-decomposable group; and $R^{21}$ and $R^{22}$ represent a hydrogen atom, a halogen atom, or an alkyl group having 1 to 4 carbon atoms.

The adhesion improver is characterized by being an organosilicon compound, and the organosilicon compound is characterized by being a compound represented by the following general formula (7):

[Formula 11]

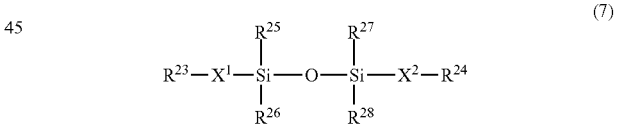

(7)

wherein $R^{23}$ to $R^{28}$ represent a monovalent organic group; and $X^1$ and $X^2$ represent a divalent organic group.

Furthermore, the present invention provides a patterning method comprising at least:

applying the above chemically amplified photosensitive resin composition on a processed substrate;

pre-baking;

exposing;

after-exposure baking;

developing; and post-baking.

The present invention provides the above patterning method characterized by further comprising post-exposing between the developing and the post-baking.

Effects of the Invention

A (meth)acrylamide derivative of the present invention can be preferably used as a raw material for polymerizing a polymer. This polymer can be preferably used for obtaining a chemically amplified photosensitive resin composition. Furthermore, a chemically amplified photosensitive resin composition and a patterning method of the present invention allow development with an alkaline developer, exhibits excellent film properties such as heat resistance, mechanical properties and electric properties, and can form a pattern with higher resolution.

Furthermore, since the polymer of the present invention has a repeating constitutional unit represented by the general formula (2), a stable benzoxazole ring can be formed by directly heating or by heating after decomposition of an acid-decomposable group with an acid.

Since the benzoxazole ring is formed by heating an interlayer insulating film and a surface protection film using the chemically amplified photosensitive resin composition of the present invention containing the polymer, the films have excellent film properties such as heat resistance, mechanical properties and electric properties.

BEST MODE FOR CARRYING OUT THE INVENTION

A (meth)acrylamide derivative, a polymer, a chemically amplified photosensitive resin composition and a patterning method in accordance with the present invention will be sequentially described.

<(Meth)Acrylamide Derivative>

A (meth)acrylamide derivative of the present invention is represented by the following general formula (1):

[Formula 12]

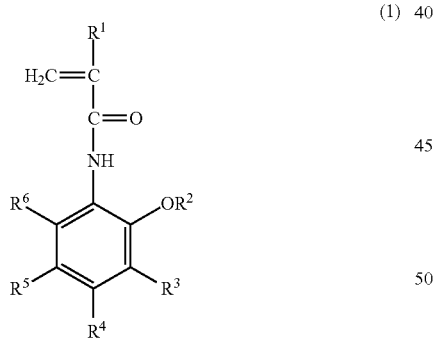
(1)

In the formula (1),
$R^1$ represents a hydrogen atom or a methyl group;
$R^2$ represents an acid-decomposable group; and
$R^3$ to $R^6$ independently represent a hydrogen atom, a halogen atom or an alkyl group having 1 to 4 carbon atoms.

Examples of the acid-decomposable group include a t-butyl group, a tetrahydropyran-2-yl group, a tetrahydrofuran-2-yl group, a 4-methoxytetrahydropyran-4-yl group, a 1-ethoxyethyl group, a 1-butoxyethyl group, a 1-propoxyethyl group, a methoxymethyl group, an ethoxymethyl group and a t-butoxycarbonyl group.

Examples of the halogen atom include a fluorine atom and a chlorine atom.

Examples of the alkyl group having 1 to 4 carbon atoms include a methyl group, an ethyl group, a n-propyl group, an isopropyl group, a n-butyl group and a tert-butyl group.

Specific examples of the (meth)acrylamide derivative represented by the general formula (1) include, but not limited to, the following compounds shown in Table 1.

TABLE 1

A-1

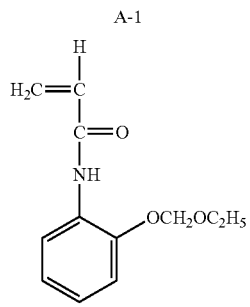

A-2

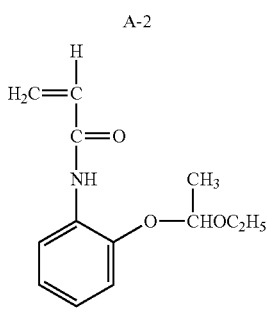

A-3

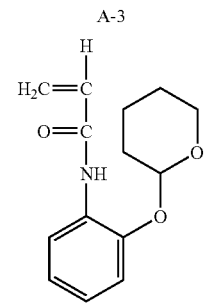

A-4

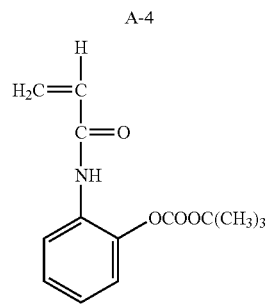

TABLE 1-continued
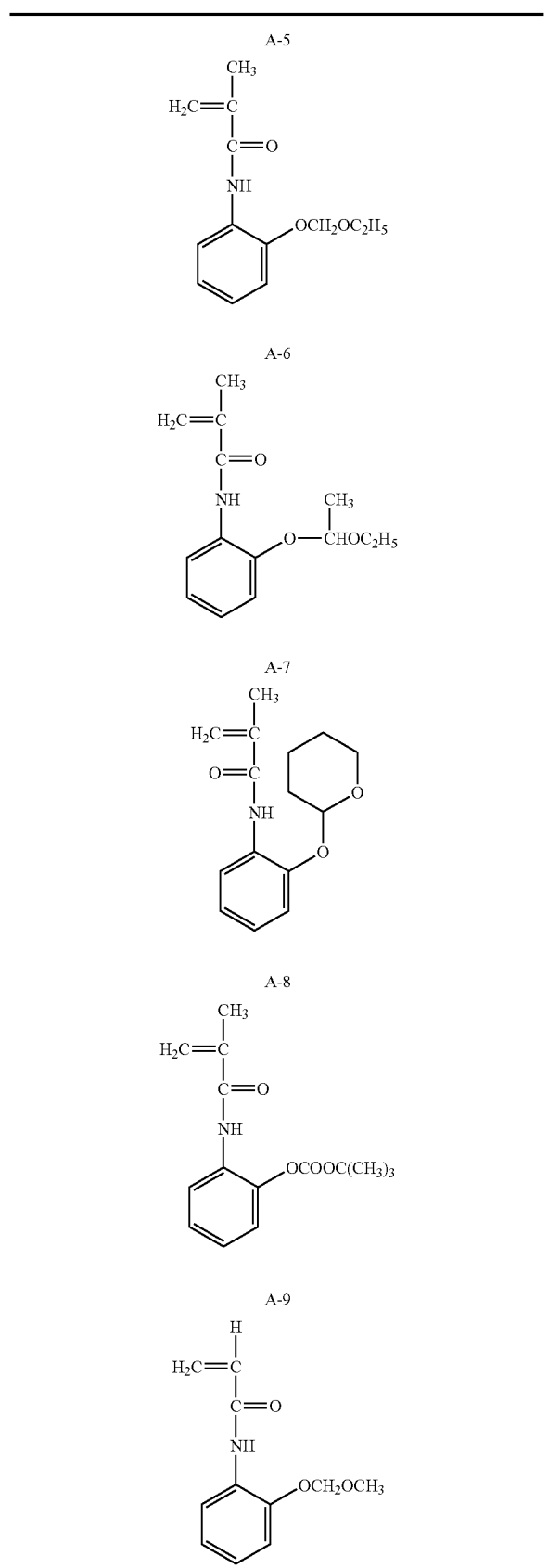
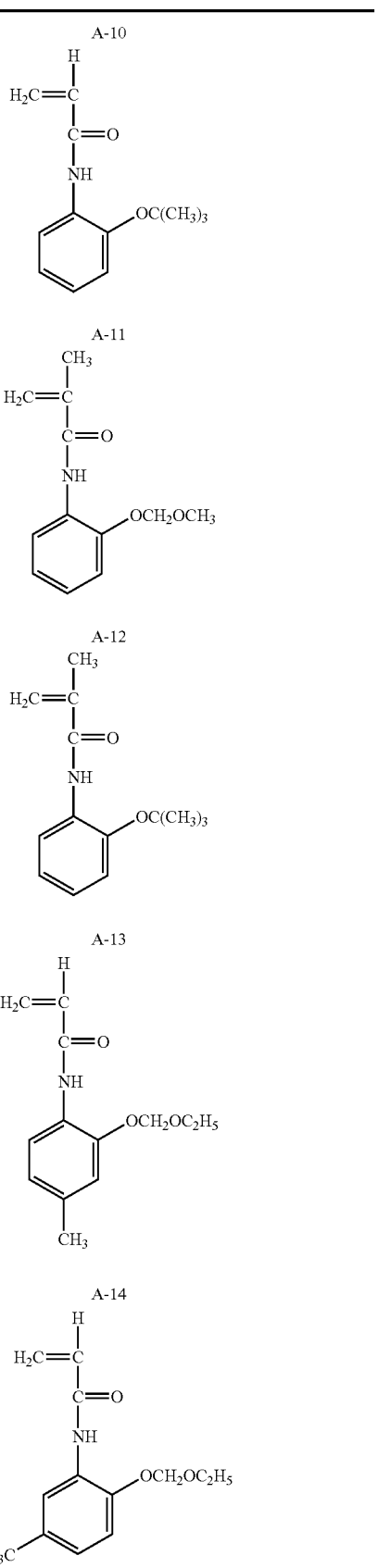

TABLE 1-continued

A-15

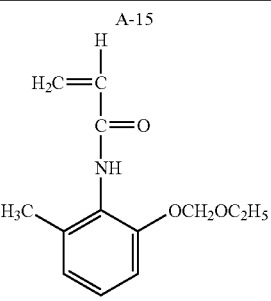

The above compounds are named as following:
A-1: N-(2-ethoxymethoxyphenyl)acrylamide,
A-2: N-(2-(1-ethoxyethoxy)phenyl)acrylamide,
A-3: N-(2-(tetrahydropyran-2-yloxy)phenyl)acrylamide,
A-4: N-(2-t-butoxycarbonyloxyphenyl)acrylamide,
A-5: N-(2-ethoxymethoxyphenyl)methacrylamide,
A-6: N-(2-(1-ethoxyethoxy)phenyl)methacrylamide,
A-7: N-(2-(tetrahydropyran-2-yloxy)phenyl)methacrylamide,
A-8: N-(2-t-butoxycarbonyloxyphenyl)methacrylamide,
A-10: N-(2-t-butoxyphenyl)acrylamide,
A-11: N-(2-methoxymethoxyphenyl)methacrylamide,
A-12: N-(2-t-butoxyphenyl)methacrylamide,
A-13: N-(2-ethoxymethoxy-4-methylphenyl)acrylamide,
A-14: N-(2-ethoxymethoxy-5-methylphenyl)acrylamide,
A-15: N-(2-ethoxymethoxy-6-methylphenyl)acrylamide.

Since a stable benzoxazole ring is formed by heating a polymer of each of these (meth)acrylamide derivatives alone or a polymer with the other copolymerizable monomer or by heating after decomposition of an acid-decomposable group with an acid after forming a pattern, a film having excellent properties such as heat resistance, mechanical properties and electric properties can be formed.

Among the (meth)acrylamide derivatives represented by the general formula (1), a compound (the above compound A-1) in which $R^1$ is a hydrogen atom; $R^2$ is an ethoxymethyl group; and $R^3$ to $R^6$ are a hydrogen atom can be synthesized, for example, by the following manner. In this manner, o-aminophenol is reacted with acryloyl chloride in N-methyl-2-pyrrolidone (NMP) in the presence of lithium chloride to obtain N-(2-hydroxyphenyl)acrylamide. N-(2-hydroxyphenyl)acrylamide is then reacted with chloromethyl ethyl ether in NMP in the presence of N,N-diisopropyl ethylamine to synthesize the above compound A-1.

<Polymer>

A polymer of the present invention contains repeating constitutional units represented by the general formula (2):

[Formula 13]

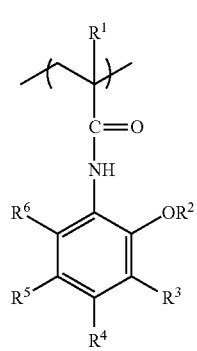

(2)

In the formula (2), $R^1$ represents a hydrogen atom or a methyl group;

$R^2$ represents an acid-decomposable group; and $R^3$ to $R^6$ independently represent a hydrogen atom, a halogen atom or an alkyl group having 1 to 4 carbon atoms.

Examples of the acid-decomposable group include a t-butyl group, a tetrahydropyran-2-yl group, a tetrahydrofuran-2-yl group, a 4-methoxytetrahydropyran-4-yl group, a 1-ethoxyethyl group, a 1-butoxyethyl group, a 1-propoxyethyl group, a methoxymethyl group, an ethoxymethyl group and a t-butoxycarbonyl group.

Examples of the halogen atom include fluorine atom and chlorine atom.

Examples of the alkyl group having 1 to 4 carbon atoms include a methyl group, an ethyl group, a n-propyl group, an isopropyl group, a n-butyl group and a tert-butyl group.

Examples of the repeating constitutional unit represented by the general formula (2) include, but not limited to, the following example as shown in Table 2:

TABLE 2

B-1

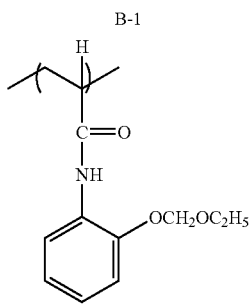

B-2

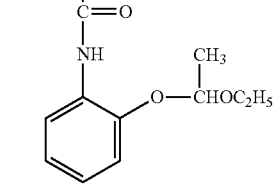

B-3

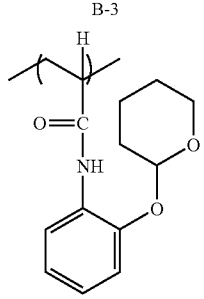

TABLE 2-continued
B-4
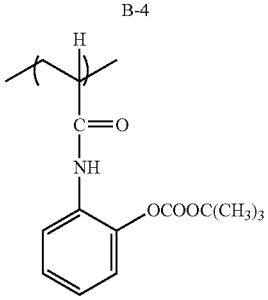
B-5
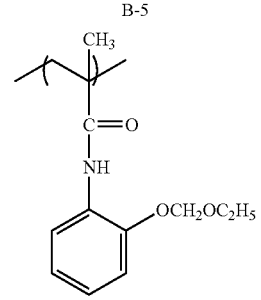
B-6
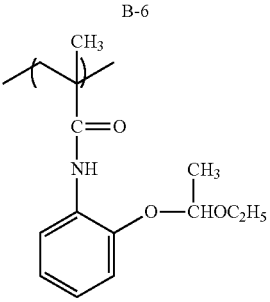
B-7
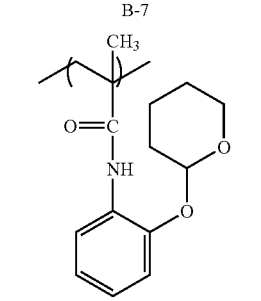
B-8
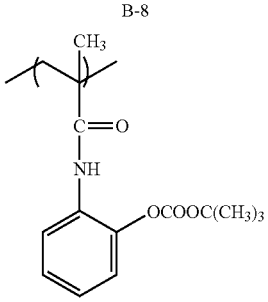
B-9
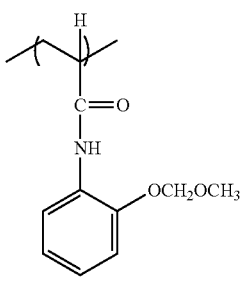
B-10
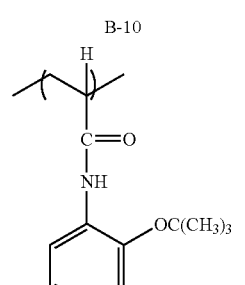
B-11
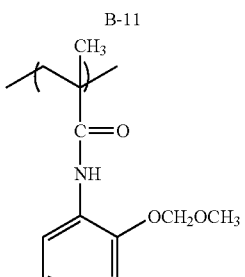
B-12
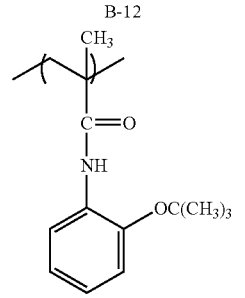
B-13
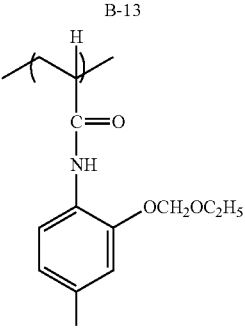

TABLE 2-continued

B-14

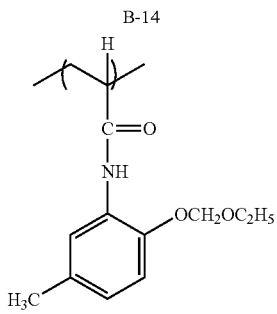

B-15

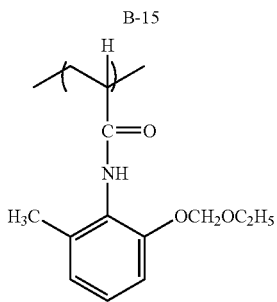

The above polymers having the repeating constitutional unit of 100% are named as following:

B-1: poly[N-(2-ethoxymethoxyphenyl)acrylamide],
B-2: poly[N-(2-(1-ethoxyethoxy)phenyl)acrylamide],
B-3: poly[N-(2-(tetrahydropyran-2-yloxy)phenyl)acrylamide],
B-4: poly[N-(2-t-butoxycarbonyloxyphenyl)acrylamide],
B-5: poly[N-2-ethoxymethoxyphenyl)methacrylamide],
B-6: poly[N-(2-(1-ethoxyethoxy)phenyl)methacrylamide],
B-7: poly[N-(2-(tetrahydropyran-2-yloxy)phenyl)methacrylamide],
B-8: poly[N-(2-t-butoxycarbonyloxyphenyl)methacrylamide],
B-9: poly[N-(2-methoxymethoxyphenyl)acrylamide],
B-10: poly[N-(2-t-butoxyphenyl)acrylamide],
B-11: poly[N-(2-methoxymethoxyphenyl)methacrylamide],
B-12: poly[N-(2-t-butoxyphenyl)methacrylamide],
B-13: poly[N-(2-ethoxymethoxy-4-methylphenyl)acrylamide],
B-14: poly[N-(2-ethoxymethoxy-5-methylphenyl)acrylamide],
B-15: poly[N-(2-ethoxymethoxy-6-methylphenyl)acrylamide].

The polymer of the present invention is heated or heated after decomposition of the acid-decomposable group with an acid after patterning to induce a ring-closing reaction to form a benzoxazole ring.

For example, an acrylamide polymer having a group A which is an acid-decomposable group induces a ring-closing reaction by heating or heating after decomposing the acid-decomposable group with an acid to form a benzoxazole ring as shown in the following reaction scheme B.

REACTION SCHEME B

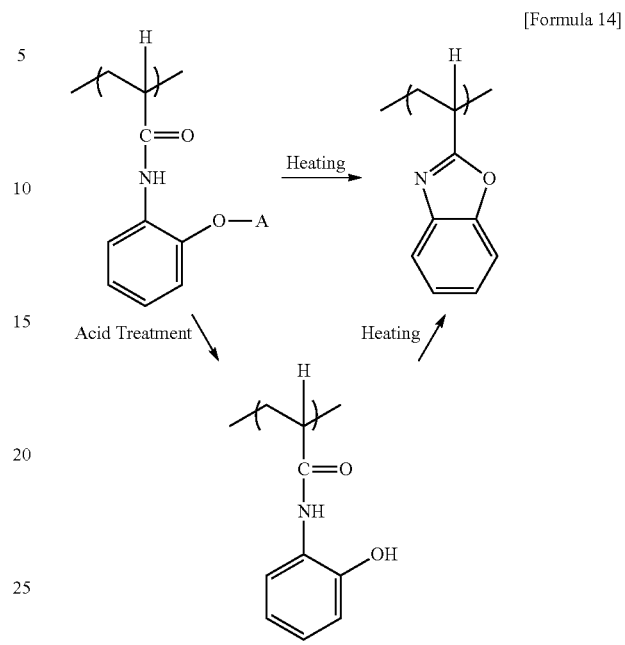

[Formula 14]

Since this benzoxazole ring is a stable structure, this polymer can be used for an interlayer insulating film or surface protection film, to provide an interlayer insulating film or surface protection film having excellent film properties such as heat resistance, mechanical properties and electric properties.

A raw material for the polymer of the present invention is not limited so far as a polymer containing the repeating constitutional unit represented by the general formula (2) can be synthesized, and so can be suitably selected from the (meth)acrylamide derivatives represented by the general formula (1).

A polymer of the present invention may be used what is obtained by homopolymerizing the (meth)acrylamide derivative alone represented by the general formula (1) or by copolymerizing the (meth)acrylamide derivative with a comonomer. As a copolymer prepared by copolymerization of the above (meth)acrylamide derivative and a comonomer imparts properties of the comonomer thereto, the polymer is improved properties (e.g., resolution and sensitivity) useful for a chemically amplified photosensitive resin composition containing the polymer and properties (e.g., heat resistance, mechanical properties and electric properties) useful for an interlayer insulating film or surface protection film formed from a photosensitive resin by using various comonomers.

A comonomer is preferably a vinyl monomer because it is sufficiently polymerizable with the (meth)acrylamide derivative. Examples of the vinyl monomer include (meth)acrylamide derivatives other than the above (meth)acrylamide derivative, butadiene, acrylonitrile, styrene, (meth)acrylic acid, ethylene derivatives, styrene derivatives, (meth)acrylate derivatives.

Examples of the ethylene derivative include ethylene, propylene and vinyl chloride. Examples of the styrene derivative include α-methylstyrene, p-hydroxystyrene, chlorostyrene, and a styrene derivative described in Japanese Patent Laid-Open No. 2001-172315.

In addition to a vinyl monomer, maleic anhydride and N-phenylmaleimide derivatives may be used. Examples of the N-phenylmaleimide derivative include N-phenylmaleimide and N-(4-methylphenyl)maleimide. One or more of these comonomers can be used.

Specific examples of the constitutional unit from the comonomer of the above copolymer include a constitutional units derived from a (meth)acrylamide derivative represented by the following general formula (3) and a (meth)acrylate having a lactone ring represented by the following general formula (4):

[Formula 15]

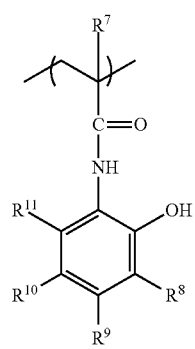

(3)

In the formula (3),
$R^7$ represents a hydrogen atom or a methyl group; and
$R^8$ to $R^{11}$ independently represent a hydrogen atom, a halogen atom or an alkyl group having 1 to 4 carbon atoms.

[Formula 16]

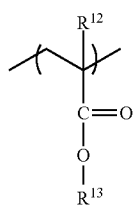

(4)

In the formula (4),
$R^{12}$ represents a hydrogen atom or a methyl group, and
$R^{13}$ represents an organic group having a lactone structure.
Examples of the repeating constitutional unit represented by the general formula (4) include, but not limited to, examples as shown in the following Table 3.

TABLE 3

C-1
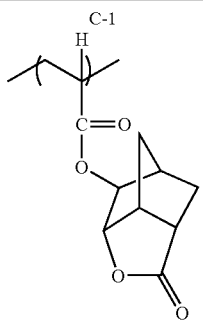

TABLE 3-continued

C-2
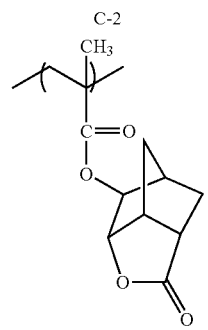

C-3
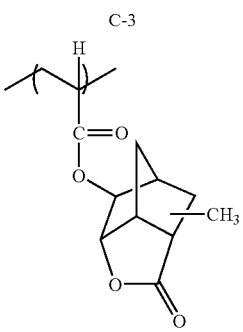

C-4
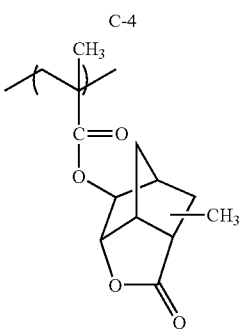

C-5
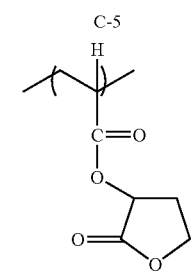

C-6
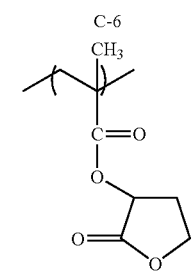

TABLE 3-continued

C-7
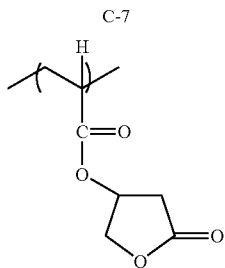

C-8
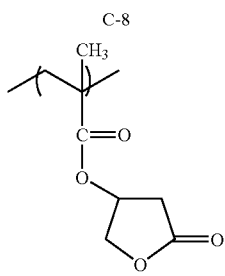

C-9
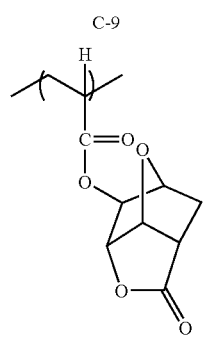

C-10
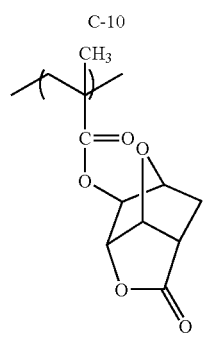

C-11
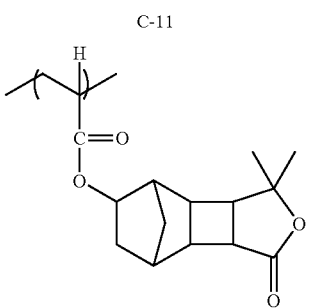

TABLE 3-continued

C-12
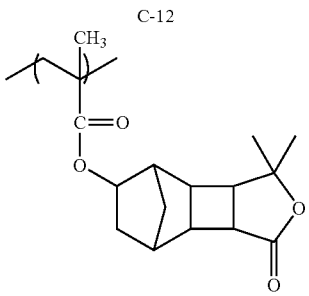

For achieving excellent film properties when the polymer of the present invention is used for an interlayer insulating film or surface protection film, the content of the repeating constitutional unit represented by the general formula (2) in the polymer is preferably 10 to 100 mol %, more preferably 20 to 100 mol %.

The weight average molecular weight (Mw) of the polymer is preferably 2,000 to 200,000, more preferably 4,000 to 100,000. If the weight average molecular weight of the polymer is less than 2,000, it may be difficult to form a homogeneous film when the polymer is used for the interlayer insulating film or the surface protection film. If the weight average molecular weight of the polymer is more than 200,000, resolution may be deteriorated when the polymer is used for the interlayer insulating film or the surface protection film.

Such a polymer can be prepared by polymerizing the monomer composition containing the above (meth)acrylamide derivative via a commonly used polymerization process such as radical polymerization and anion polymerization.

For example, when a polymer is prepared by the radical polymerization, an appropriate radical polymerization initiator such as 2,2'-azobis(isobutyronitrile) is added to a dry tetrahydrofuran in which the monomer composition containing the above (meth)acrylamide derivative is dissolved, and the mixture can be then stirred at 50 to 70° C. for 0.5 to 24 hours under an atmosphere of an inert gas such as argon and nitrogen to give the polymer.

<Chemically Amplified Photosensitive Resin Composition>

A chemically amplified photosensitive resin composition of the present invention comprises at least a polymer and a photoacid generator, the polymer containing at least one constitutional unit selected from the group consisting of a repeating constitutional unit represented by the following general formula (2) and a repeating constitutional unit represented by the following general formula (3), and can be generally prepared by mixing the above polymer with the photoacid generator:

[Formula 17]

(2)
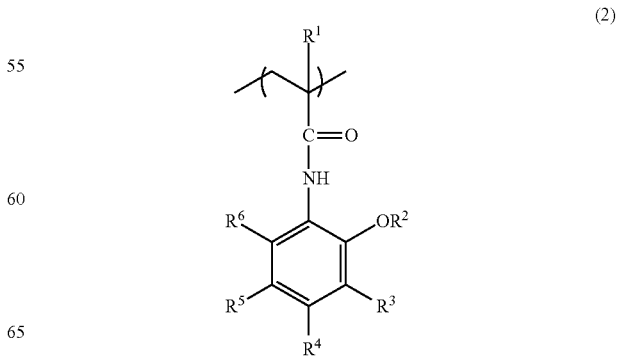

wherein,

R¹ represents a hydrogen atom or a methyl group;

R² represents an acid-decomposable group; and

R³ to R⁶ independently represent a hydrogen atom, a halogen atom or an alkyl group having 1 to 4 carbon atoms;

[Formula 18]

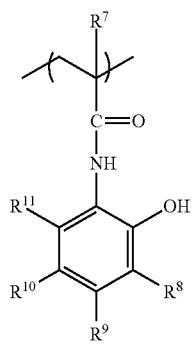

(3)

wherein,

R⁷ represents a hydrogen atom or a methyl group; and

R⁸ to R¹¹ independently represent a hydrogen atom, a halogen atom or an alkyl group having 1 to 4 carbon atoms.

When the chemically amplified photosensitive resin composition containing the polymer having the repeating constitutional unit represented by the above general formula (2) is patterned by exposure with chemical rays as described later, an acid is generated from the photoacid generator constituting the chemically amplified photosensitive resin composition of an exposed area. The acid is reacted with the acid-decomposable group in the resin, and the acid-decomposable group causes a decomposition reaction. As a result, the polymer of the present invention can be solved in the alkaline developer in the exposed area, resulting in a solubility difference ("solubility contrast") between the exposed area and the unexposed area. Patterning using the chemically amplified photosensitive resin composition is carried out utilizing such a solubility difference in the alkaline developer.

On the other hand, the chemically amplified photosensitive resin composition using a polymer having no repeating constitutional unit represented by the general formula (2) should contain the dissolution inhibitor as described later in order to express the solubility contrast. In that case, when the chemically amplified photosensitive resin composition is patterned by exposure with chemical rays as described later, an acid is generated from the photoacid generator constituting the chemically amplified photosensitive resin composition of the exposed area. The acid is reacted with the acid-decomposable group in the dissolution inhibitor, and the acid-decomposable group causes a decomposition reaction. As a result, the resin composition, can be solved in the alkaline developer in the exposed area, resulting in a solubility difference ("solubility contrast") between the exposed area and the unexposed area. Therefore, even the patterning using the chemically amplified photosensitive resin composition is carried out utilizing the solubility difference in the alkaline developer as well as the case of the chemically amplified photosensitive resin composition using the polymer having the repeating constitutional unit represented by the general formula (2).

A photoacid generator preferably generates an acid by irradiation with light used for exposing. As long as the photoacid generator may be any of those whose mixture with a polymer of the present invention is adequately soluble in an organic solvent and the solution obtained can be used to form a homogeneous coating film by a film forming method such as spin coating, the photoacid generator is not particularly limited. The photoacid generator may be used alone or in combination with two or more.

Examples of the photoacid generator include triarylsulfonium salt derivatives, diaryliodonium salt derivatives, dialkylphenacylsulfonium salt derivatives, nitrobenzyl sulfonate derivatives, sulfonate derivatives of N-hydroxynaphthalimide and sulfonate derivatives of N-hydroxysuccinimide, but not limited to those.

The content of the photoacid generator is preferably not less than 0.2% by mass, more preferably not less than 1% by mass to the total of the polymer and photoacid generator in view of achieving adequate sensitivity of the chemically amplified photosensitive resin composition and satisfactory patterning. On the other hand, it is preferably not more than 30% by mass, more preferably not more than 15% by mass in view of forming a homogeneous coating film and preventing a residue (scum) after development.

An appropriate solvent may be, if necessary, used in preparation of the chemically amplified photosensitive resin composition of the present invention.

As the solvent, any organic solvent may be used without limitations as long as it can adequately dissolve the chemically amplified photosensitive resin composition, a resultant solution can be used to form a homogeneous film by, for example, spin coating. Specific examples include γ-butyrolactone, propylene glycol monomethyl ether acetate, propylene glycol monoethyl ether acetate, ethyl lactate, 2-heptanone, 2-methoxybutyl acetate, 2-ethoxyethyl acetate, methyl pyruvate, ethyl pyruvate, methyl 3-methoxypropionate, ethyl 3-methoxypropionate, N-methyl-2-pyrrolidone (NMP), cyclohexanone, cyclopentanone, methyl isobutyl ketone (MIBK), ethylene glycol monomethyl ether, ethylene glycol monomethyl ether acetate, ethylene glycol monoethyl ether, ethylene glycol monoisopropyl ether, diethylene glycol monomethyl ether and diethylene glycol dimethyl ether, which may be used alone or in combination of two or more.

Furthermore, the chemically amplified photosensitive resin composition may contain, if necessary, other components such as a dissolution promoter, a dissolution inhibitor, an adhesion improver, a surfactant, a pigment, a stabilizer, a coating modifier and a dye.

For example, the dissolution of the unexposed area of the photosensitive resin to the alkaline developer is suppressed by adding the dissolution inhibitor to the chemically amplified photosensitive resin composition. On the other hand, in the exposed area, the acid-decomposable group in the structure of the dissolution inhibitor is also decomposed by the operation of the acid generated from the photoacid generator constituting the chemically amplified photosensitive resin composition to increase the solubility to the alkaline developer. As a result, the solubility contrast between the exposed area and the unexposed area can be increased to form a fine pattern.

When the dissolution inhibitor is added to the chemically amplified photosensitive resin composition, the content is preferably not less than 1% by mass relative to the total of the polymer and photoacid generator in view of enabling excellent patterning of the chemically amplified photosensitive resin composition, and more preferably not less than 5% by mass. On the other hand, the content is preferably not more than 70% by mass in order to realize the formation of a homogeneous coating film, and more preferably not more than 50% by mass.

Specific examples of the dissolution inhibitor include, but not limited to, a compound represented by the following general formula (5) or the following general formula (6):

[Formula 19]

$$R^{17}-\overset{O}{\underset{\|}{C}}-NH \underset{R^{14}O}{\underset{|}{\bigcirc}} Z \underset{OR^{15}}{\underset{|}{\bigcirc}} NH-\overset{O}{\underset{\|}{C}}-R^{16} \quad (5)$$

In the formula (5), $R^{14}$ and $R^{15}$ represent an acid-decomposable group (specifically, a t-butyl group, a tetrahydropyran-2-yl group, a tetrahydrofuran-2-yl group, a 4-methoxytetrahydropyran-4-yl group, a 1-ethoxyethyl group, a 1-butoxyethyl group, a 1-propoxyethyl group, a methoxymethyl group, an ethoxymethyl group, and a t-butoxycarbonyl group);

$R^{16}$ and $R^{17}$ are a linear, branched or cyclic alkyl group (specifically, a methyl group, an ethyl group, a butyl group, a cyclohexyl group, a norbornyl group, a 5-norbornen-2-yl group or the like) or an aromatic hydrocarbon group (a phenyl group, a tolyl group and a naphthyl group or the like) having 1 to 10 carbon atoms; and Z represents a direct bond, $-C(CF_3)_2-$, $-SO_2-$, $-CO-$, $-O-$, or a divalent hydrocarbon group (specifically, $-C(CH_3)_2-$, $-CH_2-$, an adamantanediyl group, a tricyclodecanediyl group, a norbornanediyl group, a cyclohexanediyl group, and a phenylene group or the like).

[Formula 20]

$$\underset{OR^{19}}{\underset{|}{\bigcirc^{R^{22}}}} NH-\overset{O}{\underset{\|}{C}}-R^{18}-\overset{O}{\underset{\|}{C}}-NH \underset{OR^{20}}{\underset{|}{\bigcirc^{R^{21}}}} \quad (6)$$

In the formula (6), $R^{18}$ represents a divalent hydrocarbon group (specifically, a phenylene group, a naphtylene group, an adamantanediyl group, a tricyclodecanediyl group, a norbornanediyl group and a cyclohexanediyl group or the like);

$R^{19}$ and $R^{20}$ represent an acid-decomposable group (specifically, a t-butyl group, a tetrahydropyran-2-yl group, a tetrahydrofuran-2-yl group, a 4-methoxytetrahydropyran-4-yl group, a 1-ethoxyethyl group, a 1-butoxyethyl group, a 1-propoxyethyl group, a methoxymethyl group, an ethoxymethyl group and a t-butoxycarbonyl group or the like);

$R^{21}$ and $R^{22}$ represent a hydrogen atom, a halogen atom or an alkyl group having 1 to 4 carbon atoms (specifically, a methyl group, an ethyl group, a n-propyl group, an isopropyl group, a n-butyl group and a tert-butyl group or the like).

For example, the adhesion of a photosensitive resin to a substrate can be improved by adding an adhesion improver composed of an organosilicon compound to a chemically amplified photosensitive resin composition.

Examples of the organosilicon compound include, but not limited to, γ-aminopropyltrimethoxysilane, γ-aminopropyltriethoxysilane, vinyltriethoxysilane, an organosilicon compound described in Japanese Patent Publication No. 3422703, and an organosilicon compound represented by the following general formula (7).

[Formula 21]

$$R^{23}-X^1-\underset{\underset{R^{26}}{|}}{\overset{\overset{R^{25}}{|}}{Si}}-O-\underset{\underset{R^{28}}{|}}{\overset{\overset{R^{27}}{|}}{Si}}-X^2-R^{24} \quad (7)$$

In the formula (7), $R^{25}$ to $R^{28}$ represent a monovalent organic group (specifically, a methyl group, an ethyl group, a propyl group, a butyl group and a phenyl group or the like);

$X^1$ and $X^2$ are a divalent organic group (a methylene group, an ethylene group, a propylene group, a butylene group and a phenylene group or the like); and $R^{23}$ and $R^{24}$ are a monovalent organic group (specifically, a monovalent organic group represented by the following structure):

[Formula 22]

When the adhesion improver is added to the chemically amplified photosensitive resin composition, the content is preferably not less than 0.1% by mass relative to the total of the polymer and photoacid generator in view of enabling the formation of the pattern having excellent adhesion, and more preferably not less than 0.5% by mass. Its content is preferably not more than 20% by mass in order to enable excellent resolution, and more preferably not more than 10% by mass.

The chemically amplified photosensitive resin composition of the present invention gives excellent pattern resolution and can be developed with an alkaline developer. The film consisting of the chemically amplified photosensitive resin composition of the present invention gives excellent film properties such as heat resistance, mechanical properties and electric properties. Thus, such a chemically amplified photosensitive resin composition is suitable as an interlayer insulating film or surface protection film.

<Patterning Method>

The patterning method of the present invention has at least an application step, a pre-bake step, an exposure step, an after-exposure bake step, a development step and a post-bake step. In particular, the patterning method of the present invention comprises at least: an application step of applying the chemically amplified photosensitive resin composition on a processed substrate; a pre-bake step of fixing the chemically amplified photosensitive resin composition film on the processed substrate, an exposure step of selectively exposing the chemically amplified photosensitive resin composition film; an after-exposure bake step of baking the chemically amplified photosensitive resin composition film after exposure; a development step of dissolving and removing the exposed area in the chemically amplified photosensitive resin composition film to form a pattern; and a post-bake step of curing the patterned chemically amplified photosensitive resin composition film. The patterning method of the present invention may include a post-exposure step between the development step and the post-bake step.

In the application step, the above chemically amplified photosensitive resin composition is applied on a processed substrate such as a silicon wafer and a ceramic substrate. Application may be carried out by spin coating using a spin coater, spray coating using a spray coater, immersion, printing and roll coating.

In the pre-bake step, the chemically amplified photosensitive resin composition applied on the processed substrate is dried to remove a solvent in the chemically amplified photosensitive resin composition to fix the chemically amplified photosensitive resin composition film applied on the processed substrate. The pre-bake step is generally carried out at 60 to 150° C.

In the exposure step, the chemically amplified photosensitive resin composition film is selectively exposed via a photomask to form an exposed area and an unexposed area, to transfer a pattern in a photomask to the chemically amplified photosensitive resin composition film. Chemical rays used in the pattern exposure include ultraviolet rays, visible light ray, Excimer laser, electron beam ray and X-ray, and preferably chemical rays having a wavelength of 180 to 500 nm.

The after-exposure bake step promotes the reaction between the acid generated by exposing and the acid-decomposable group of the polymer. The after-exposure bake step is generally carried out at 60 to 150° C.

In the development step, an exposed area in the chemically amplified photosensitive resin composition film is dissolved and removed in an alkaline developer to form a pattern. The above exposure step generates solubility difference (solubility contrast) of a polymer in an alkaline developer between an exposed area and an unexposed area in the chemically amplified photosensitive resin composition film. Utilizing the solubility contrast, the exposed area in the chemically amplified photosensitive resin composition film is removed by dissolution to obtain the chemically amplified photosensitive resin composition film having a pattern formed (hereinafter, simply referred to "pattern"). Examples of the alkaline developer include an aqueous solution of a quaternary ammonium salt such as tetramethylammonium hydroxide (TMAH) and tetraethylammonium hydroxide or an aqueous solution prepared by adding an appropriate amount of an additive such as water-soluble alcohols containing methanol and ethanol and surfactants to the above solution. Development may be carried out by, for example, paddling, immersing and spraying. After development, the pattern formed is rinsed with water.

In the post-bake step, the pattern obtained is heated in the air or under an atmosphere of an inert gas such as nitrogen, to improve adhesiveness of the pattern to the processed substrate and to cure the pattern. In the post-bake process, by heating the pattern formed in the chemically amplified photosensitive resin composition, a polymer constituting the chemically amplified photosensitive resin composition is changed in structure (denatures), and a benzoxazole ring is formed therein, to cure the pattern. Thus, a pattern having excellent film properties such as heat resistance, mechanical properties and electric properties can be obtained. The post-bake step is generally carried out at 100 to 380° C. The post-bake step may be done in one step or in multiple steps.

The post-exposure step exposes the whole surface of the chemically amplified photosensitive resin composition film having the formed pattern, and promotes the curing of the pattern in the subsequent post-bake step. Chemical rays used for the post-exposure step may be the same as that used in the above exposure step, and the chemical rays having a wavelength of 180 to 500 nm are preferable.

EXAMPLES

Hereinafter, the present invention will be more specifically explained by Examples.

Synthetic Example 1

Synthesis of N-(2-hydroxyphenyl)acrylamide 20 g of o-amino phenol was dissolved in 200 mL of N-methyl-2-pyrrolidone (NMP), and then the solution was ice-cooled. To the solution was added 8.546 g (1.1 times in mol) of lithium chloride. After lithium chloride was entirely dissolved, 17.42 g (1.05 times in mol) of acryloyl chloride was dropped into the solution, and the solution was stirred under ice-cooling for 5 hours. The reaction mixture was poured into 1.8 L of water, and an organic layer was extracted with 700 mL of diethyl ether. The diethyl ether layer was sequentially washed with 0.2 N hydrochloric acid, brine and water, and dried over magnesium sulfate. Diethyl ether was evaporated off under a reduced pressure. 80 mL of diisopropyl ether was added to the solidified residue, and the solution was heated and stirred to wash and filter the residue. The same washing process was carried out once again to obtain 10.2 g of N-(2-hydroxyphenyl)acrylamide as white powder (yield: 34%).

Example 1

Synthesis of N-(2-ethoxymethoxyphenyl)acrylamide (an acrylamide derivative: A-1 in Table 1; in the general formula (1), $R^1$ is a hydrogen atom, $R^2$ is an ethoxymethyl group, and $R^3$ to $R^6$ are a hydrogen atom)

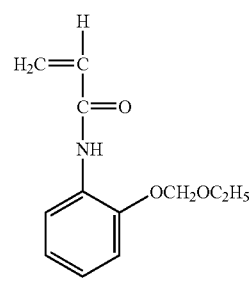

[Formula 23]

20 g of N-(2-hydroxyphenyl)acrylamide and 23.76 g of N,N-diisopropyl ethylamine were dissolved in 150 mL of NMP, and to the solution was added 12.75 g of chloromethyl ethyl ether. The solution was stirred at room temperature. The solution was poured into 1000 mL of water after 3 days, and an organic layer was extracted with 400 mL of ethyl ether. The organic layer was sequentially washed with 0.2 N hydrochloric acid, brine, 3% aqueous sodium hydroxide solution and brine. The organic layer was dried over magnesium sulfate, and then diethyl ether was evaporated off under a reduced pressure. The residue was recrystallized with hexane/ethyl acetate (100/4) to obtain 13.23 g of the desired product (white solid, yield: 49%).

$^1$H-NMR (THF-$d_8$, δ): 1.19 (3H, t), 3.72 (2H, q), 5.27 (2H, s), 5.63 (1H, dd), 6.32 (1H, dd), 6.45 (1H, dd), 6.90-6.97 (2H, m), 7.15-7.17 (1H, m), 8.35-8.50 (2H, br).

Example 2

Synthesis of N-(2-(1-ethoxyethoxy)phenyl)acrylamide (an acrylamide derivative: A-2 in Table 1; in the general formula (1), $R^1$ is a hydrogen atom, $R^2$ is an ethoxyethyl group, and $R^3$ to $R^6$ are a hydrogen atom)

[Formula 24]

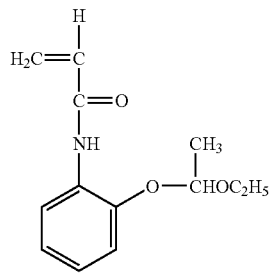

10 g of N-(2-hydroxyphenyl)acrylamide and 11.05 g of ethyl vinyl ether were dissolved in 50 mL of NMP, and to the solution was added 0.308 g of a p-toluenesulfonic acid pyridinium salt. The solution was stirred at room temperature. The reaction mixture was poured into 300 mL of water after 6 days, and an organic layer was extracted with 300 mL of diethyl ether. The organic layer was sequentially washed with 3% aqueous sodium hydroxide solution and brine. The organic layer was dried over magnesium sulfate, and then the solvent was evaporated off under a reduced pressure to obtain 9.6 g of the desired product (yield: 67%).

$^1$H-NMR (THF-$d_8$, δ): 1.20 (3H, t), 1.53 (3H, d), 3.5-3.8 (2H, m), 5.38 (1H, q), 5.75 (1H, d), 6.29 (1H, dd), 6.41 (1H, d), 7.0-7.08 (3H, m), 8.10 (1H, br), 8.48 (1H, br).

Example 3

Synthesis of N-(2-(1-ethoxyethoxy)phenyl)methacrylamide (a methacrylamide derivative: A-6 in Table 1; in the general formula (1), $R^1$ is a methyl group, $R^2$ is a 1-ethoxyethyl group, and $R^3$ to $R^6$ are a hydrogen atom)

[Formula 25]

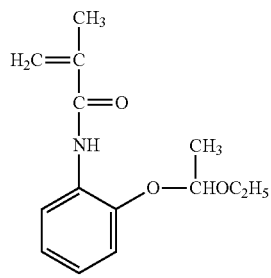

10 g of N-(2-hydroxyphenyl)methacrylamide and 10.17 g of ethyl vinyl ether were dissolved in 50 mL of NMP, and to the solution was added 0.284 g of a p-toluenesulfonic acid pyridinium salt. The solution was stirred at room temperature. The reaction mixture was poured into 300 mL of water after 6 days, and then an organic layer was extracted with 300 mL of diethyl ether. The organic layer was sequentially washed with 3% aqueous sodium hydroxide solution and brine. The organic layer was dried over magnesium sulfate, and then the solvent was evaporated off under a reduced pressure to obtain 10.2 g of the desired product (yield: 72%).

$^1$H-NMR (THF-$d_8$, δ): 1.18 (3H, t), 1.54 (3H, d), 2.08 (3H, s), 3.49-3.72 (2H, m), 5.36 (1H, q), 5.47 (1H, s), 5.87 (1H, s), 7.0-7.07 (3H, m), 8.4-8.49 (2H, m).

Example 4

Synthesis of polymer having 50 mmol % of a constitutional unit (B-1 in Table 2) in which $R^1$ is a hydrogen atom, $R^2$ is an ethoxymethyl group and $R^3$ to $R^6$ are hydrogen atoms in the general formula (2), and 50 mol % of a constitutional unit in which $R^7$ to $R^{11}$ are hydrogen atoms in the general formula (3) (following, the numbers attached to the repeating unit represent mol %)

[Formula 26]

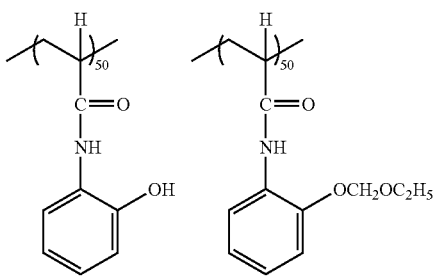

In 50 mL of tetrahydrofuran were dissolved 9 g of the acrylamide derivative obtained in the Example 1 and 12.2 g of N-(2-hydroxyphenyl)acrylamide. To the solution was added 0.181 g of 2,2'-azobis(isobutyronitrile), and the mixture was heated at reflux under an argon atmosphere for 6 hours. After cooled, it was re-precipitated in 500 mL of diethyl ether. The precipitated polymer was filtered and again purified by re-precipitation, to give 17.91 g of the desired polymer (yield: 84%).

GPC analysis: Weight average molecular weight (Mw) of the polymer 35800 (as polystyrene), Dispersion (Mw/Mn) of the polymer 3.72.

Example 5

Synthesis of polymer having 50 mol % of a constitutional unit (B-1 in Table 2) in which $R^1$ is a hydrogen atom, $R^2$ is an ethoxymethyl group and $R^3$ to $R^6$ are hydrogen atoms in the general formula (2), and 50 mol % of a constitutional unit in which $R^7$ is a methyl group and $R^8$ to $R^{11}$ are hydrogen atoms in the general formula (3) (following, the numbers attached to the repeating unit represent mol %)

[Formula 27]

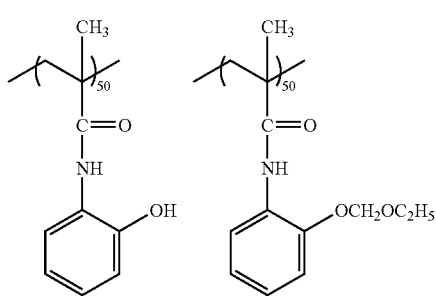

The polymerization was carried out in the same manner as in the Example 4 except that 13.25 g of N-(2-hydroxyphenyl) methacrylamide was used in place of N-(2-hydroxyphenyl) acrylamide to give 17.58 g of the desired polymer (yield: 79%)

GPC analysis: Weight average molecular weight (Mw) 32100 (as polystyrene), Dispersion (Mw/Mn) 3.65.

Example 6

Synthesis of polymer having 50 mol % of a constitutional unit (B-2 in Table 2) in which $R^1$ is a hydrogen atom, $R^2$ is a 1-ethoxyethyl group and $R^3$ to $R^6$ are hydrogen atoms in the general formula (2), and 50 mol % of a constitutional unit in which $R^7$ to $R^{11}$ are hydrogen atoms in the general formula (3) (following, the numbers attached to the repeating unit represent mol %)

[Formula 28]

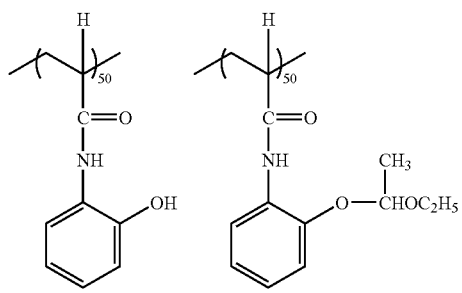

The polymerization was carried out in the same manner as in the Example 4 except that 9.57 g of the acrylamide derivative obtained in the Example 2 was used in place of the (meth)acrylamide derivative obtained in the Example 1 to give 17.42 g of the desired polymer (yield: 80%).

GPC analysis: Weight average molecular weight (Mw) 37500 (as polystyrene), Dispersion (Mw/Mn) 3.78.

Example 7

Synthesis of polymer having 50 mol % of a constitutional unit (B-6 in Table 2) in which $R^1$ is a methyl group, $R^2$ is a 1-ethoxyethyl group and $R^3$ to $R^6$ are hydrogen atoms in the general formula (2), and 50 mol % of a constitutional unit in which $R^7$ to $R^{11}$ are hydrogen atoms in the general formula (3) (following, the numbers attached to the repeating unit represent mol %)

[Formula 29]

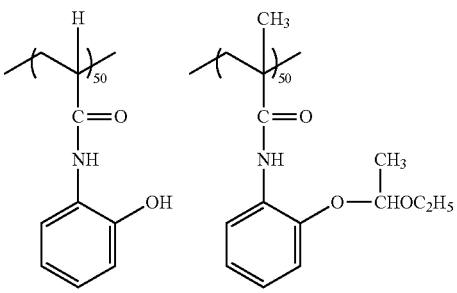

The polymerization was carried out in the same manner as in the Example 4 except that 10.14 g of the methacrylamide derivative obtained in the Example 3 was used in place of the acrylamide derivative obtained in the Example 1 to give 17.2 g of the desired polymer (yield: 77%).

GPC analysis: Weight average molecular weight (Mw) 32600 (as polystyrene), Dispersion (Mw/Mn) 3.58.

Example 8

Synthesis of polymer having 50 mol % of a constitutional unit (B-1 in Table 2) in which $R^1$ is a hydrogen atom, $R^2$ is an ethoxymethyl group and $R^3$ to $R^6$ are hydrogen atoms in the general formula (2), 35 mol % of a constitutional unit in which $R^7$ to $R^{11}$ are hydrogen atoms in the general formula (3), and 15 mol % of a constitutional unit based on styrene (following, the numbers attached to the repeating unit represent mol %)

[Formula 30]

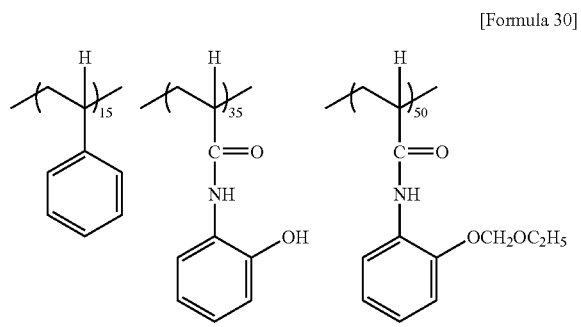

In 50 mL of tetrahydrofuran were dissolved 10 g of the acrylamide derivative obtained in the Example 1, 9.49 g of N-(2-hydroxyphenyl)acrylamide and 1.91 g of styrene. To the solution was added 0.181 g of 2,2'-azobis(isobutyronitrile), and the mixture was heated at reflux under an argon atmosphere for 6 hours. After cooled, it was re-precipitated in 500 mL of diethyl ether. The precipitated polymer was filtered and again purified by re-precipitation, to give 18.4 g of the desired polymer (yield: 86%).

GPC analysis: Weight average molecular weight (Mw) 28600 (as polystyrene), Dispersion (Mw/Mn) 3.88

Example 9

Synthesis of polymer having 50 mol % of a constitutional unit (B-1 in Table 2) in which $R^1$ is a hydrogen atom, $R^2$ is an ethoxymethyl group and $R^3$ to $R^6$ are hydrogen atoms in the general formula (2), 30 mol % of a constitutional unit in which $R^7$ to $R^{11}$ are hydrogen atoms in the general formula (3), and 20 mol % of a constitutional unit (C-1 in Table 3) in which $R^{13}$ is a 2,6-norbornane lactone-5-yl group in the general formula (4) (following, the numbers attached to the repeating unit represent mol %)

[Formula 31]

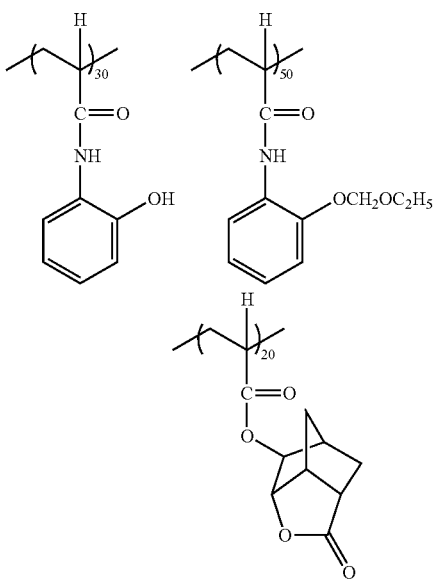

In 119 mL of tetrahydrofuran were dissolved 28 g of the acrylamide derivative obtained in the Example 1, 12.39 g of N-(2-hydroxyphenyl)acrylamide and 10.54 g of 5-acroyloxy-2,6-norbornane lactone. To the solution was added 0.416 g of 2,2'-azobis(isobutyronitrile), and the mixture was heated at reflux under an argon atmosphere for 4 hours. After allowing it to be cooled, it was re-precipitated in 1000 mL of diethyl ether. The precipitated polymer was filtered and again purified by re-precipitation, to give 48.79 g of the desired polymer (yield: 96%).

GPC analysis: Weight average molecular weight (Mw) 29000 (as polystyrene), Dispersion (Mw/Mn) 3.32.

Example 10

Synthesis of polymer having 65 mol % of a constitutional unit (B-1 in Table 2) in which $R^1$ is a hydrogen atom, $R^2$ is an ethoxymethyl group and $R^3$ to $R^6$ are hydrogen atoms in the general formula (2) and 35 mol % of a constitutional unit (C-1 in Table 3) in which $R^{13}$ is a 2,6-norbornane lactone-5-yl group in the general formula (4) (following, the numbers attached to the repeating unit represent mol %)

[Formula 32]

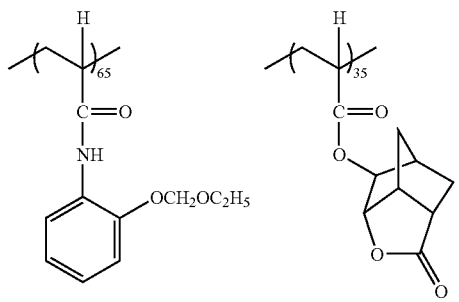

In 45 mL of tetrahydrofuran were dissolved 10 g of the acrylamide derivative obtained in the Example 1 and 5.07 g of 5-acroyloxy-2,6-norbornane lactone. To the solution was added 0.114 g of 2,2'-azobis(isobutyronitrile), and the mixture was heated at reflux under an argon atmosphere for 4 hours. After cooled, it was re-precipitated in 400 mL of diethyl ether. The precipitated polymer was filtered and again purified by re-precipitation, to give 12.81 g of the desired polymer (yield: 85%).

GPC analysis: Weight average molecular weight (Mw) 32400 (as polystyrene), Dispersion (Mw/Mn) 3.32.

Synthetic Example 2

Synthesis of 2,2-bis(4-ethoxymethoxy-3-benzamidephenyl)hexafluoropropane (a compound in which $R^{14}$ and $R^{15}$ are ethoxymethyl groups, $R^{16}$ and $R^{17}$ are phenyl groups and Z is —C(CF$_3$)$_2$— in the general formula (5), the following formula)

[Formula 33]

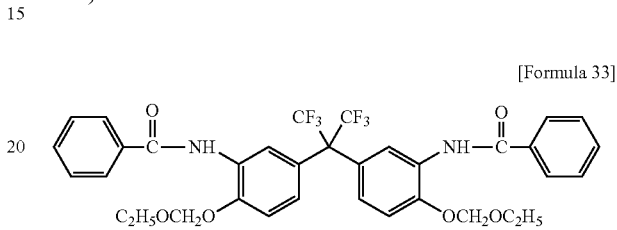

10 g of 2,2-bis(3-amino-4-hydroxyphenyl)hexafluoropropane was dissolved in 60 mL of NMP. To the solution was added 2.546 g of lithium chloride, and the solution was ice-cooled. To the solution was added 8.06 g of benzoyl chloride, and the solution was stirred under ice-cooling for 1 hours and at room temperature overnight. The reaction mixture was poured into 600 mL of water, and the precipitation was filtered and washed with water to obtain 12 g of 2,2-bis(4-hydroxy-3-benzamidephenyl)hexafluoropropane.

10 g of 2,2-bis(4-hydroxy-3-benzamidephenyl)hexafluoropropane and 6.75 g of N,N-diisopropyl ethylamine were dissolved in 60 mL of NMP, and to the solution was added 3.62 g of chloromethyl ethyl ether. The solution was stirred at room temperature for 24 hours. The reaction mixture was then poured into 600 mL of water and extracted with 300 mL of diethyl ether. The obtained ether layer was sequentially washed with 0.06 N hydrochloric acid, brine, 3% aqueous sodium hydroxide solution and brine. The ether layer was dried over magnesium sulfate, and then the solvent was evaporated off under a reduced pressure. The obtained residue was re-crystallized with hexane/ethyl acetate (5/4) to obtain 7.8 g of the desired product (white solid, yield: 65%).

$^1$H-NMR (THF-d$_8$, δ): 1.22 (6H, t); 3.79 (4H, q), 5.39 (4H, s), 7.12 (2H, d), 7.27 (2H, d), 7.45-7.55 (6H, m), 7.9-7.93 (4H, m), 8.73 (2H, s), 8.84 (2H, s).

Synthetic Example 3

Synthesis of N,N'-bis(2-ethoxymethoxyphenyl)isophthalamide (a compound in which $R^{18}$ is a phenylene group, $R^{19}$ and $R^{20}$ are ethoxymethyl groups and $R^{21}$ and $R^{22}$ are hydrogen atoms in the general formula (6), the following formula)

[Formula 34]

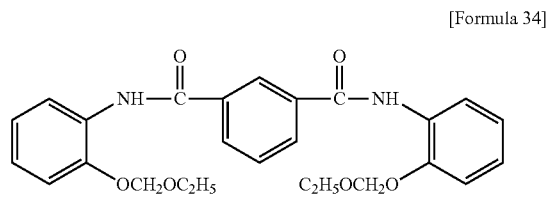

In 260 mL of NMP were dissolved 27.548 g of o-aminophenol and 11.484 g of lithium chloride. To the solution was added 25 g of isophthaloyl chloride under ice-cooling, and the solution was further stirred at room temperature overnight. The reaction mixture was then poured into water, and the precipitation was filtered and washed with water. The obtained precipitation was dissolved in 500 mL of tetrahydrofuran again and dried over magnesium sulfate. The solvent was then evaporated off under a reduced pressure to obtain 40 g of N,N'-di(2-hydroxyphenyl)isophthalamide.

40 g of N,N'-di(2-hydroxyphenyl)isophthalamide and 44.52 g of N,N-diisopropylethylamine were then dissolved in 200 mL of NMP, and to the solution was added 23.88 g of chloromethyl ethyl ether. The solution was stirred at room temperature for 3 days. The reaction mixture was then poured into 600 mL of water and extracted with 300 mL of diethyl ether. The obtained ether layer was sequentially washed with 0.06 N hydrochloric acid, brine, 3% aqueous sodium hydroxide solution and brine. The obtained ether layer was then dried over magnesium sulfate, and the solvent was evaporated off under a reduced pressure. The obtained residue was re-crystallized with hexane/ethyl acetate (5/4) twice to obtain 26 g of the desired product (white solid, yield: 49%).

$^1$H-NMR (THF-$d_8$, δ): 1.21 (6H, t), 3.78 (4H, q), 5.35 (4H, s), 6.99-7.08 (4H, m), 7.24 (2H, dd), 7.64 (1H, s), 8.12 (2H, dd), 8.45 (2H, dd), 8.52 (1H, s), 9.00 (2H, brs).

Synthetic Example 4

Synthesis of organosilicon compound having the following structure (a compound in which $R^{25}$ to $R^{28}$ are methyl groups, $X^1$ and $X^2$ are propylene groups and $R^{23}$ and $R^{24}$ are phenylmaleimide groups in the general formula (7))

[Formula 35]

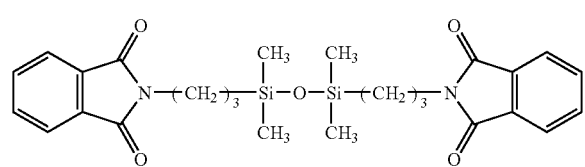

In 50 mL of NMP was dissolved 8.389 g of 1,3-bis(3-aminopropyl)tetramethyldisiloxane. To the solution was dropped 10 g of phthalic anhydride under ice-cooling and the mixture was then stirred at room temperature for one day. 300 mL of ethyl acetate was added to the reaction mixture, and the mixture was washed with brine. The mixture was dried over magnesium sulfate and the solvent was evaporated off under a reduced pressure. In 80 mL of acetic anhydride was then dissolved 18.389 g of the solidified residue, and to the solution was added 8.309 g of sodium acetate, and the solution was reacted at 90° C. for 5 hours. After cooled, it was poured into iced water and stirred for 1 hour. The precipitated crystal was filtered, and the filtered crystal was washed with water. The obtained crystal was dissolved in 200 mL of ethyl acetate, and the solution was sequentially washed with 5% sodium carbonate, brine and water, and dried over magnesium sulfate. The solvent was evaporated off under a reduced pressure; 150 mL of hexane was added to the residue; and the mixture was stirred and washed. Furthermore, the mixture was re-precipitated with hexane/ethyl acetate (5/3) to obtain 8.68 g of the desired product (white solid, total yield: 71%).

$^1$H-NMR (THF-$d_8$, δ): 0.81 (12H, s), 0.56-0.61 (4H, m), 1.67-1.75 (4H, m), 3.6-3.65 (4H, m), 7.72-7.76 (4H, m), 7.78-7.82 (4H, m).

Synthetic Example 5

Synthesis of organosilicon compound having the following structure (a compound in which $R^{25}$ to $R^{28}$ are methyl groups, $X^1$ and $X^2$ are propylene groups and $R^{23}$ and $R^{24}$ are benzamide groups in the general formula (7))

[Formula 36]

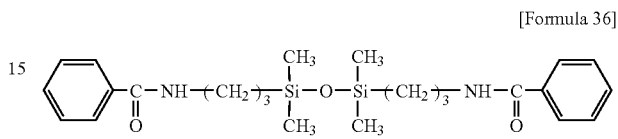

In 80 mL of tetrahydrofuran were dissolved 7.467 g of 1,3-bis(3-aminopropyl)tetramethyldisiloxane and 9.71 g of N,N-diisopropylethylamine. To the solution was dropped 8.87 g of benzoyl chloride under ice-cooling and the mixture was then stirred at room temperature for one day. Water was poured into the reaction mixture, and an organic layer was extracted with 200 mL of diethyl ether. The obtained organic layer was sequentially washed with 0.2 N hydrochloric acid, brine, 3% aqueous sodium hydroxide solution and brine. The organic layer was then dried over magnesium sulfate and evaporated off under a reduced pressure to give 8 g of the desired product as viscous liquid (yield: 58%). The obtained product was solidified by leaving the product in a refrigerator.

$^1$H-NMR (CDCl$_3$, δ): 0.06 (12H, s), 0.54-0.61 (4H, m), 1.62-1.70 (4H, m), 3.38-3.44 (4H, m), 6.78 (2H, br), 7.33-7.47 (6H, m), 7.74-7.81 (4H, m).

Synthetic Example 6

Synthesis of polymer having 65 mol % of a constitutional unit in which $R^7$ to $R^{11}$ are hydrogen atoms in the general formula (3) and 35 mol % of a constitutional unit (C-1 in Table 3) in which $R^{13}$ is a 2,6-norbornane lactone-5-yl group in the general formula (4) (following, the numbers attached to the repeating unit represent mol %)

[Formula 37]

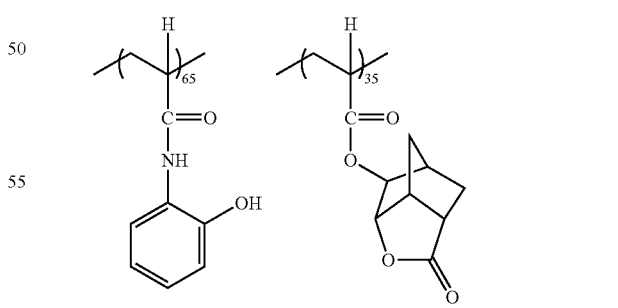

In 40 mL of tetrahydrofuran were dissolved 10 g of the acrylamide derivative obtained in the Synthetic Example 1 and 6.87 g of 5-acroyloxy-2,6-norbornane lactone. To the solution was added 0.155 g of 2,2'-azobis(isobutyronitrile), and the mixture was heated at reflux under an argon atmosphere for 4 hours. After cooled, it was re-precipitated in 400 mL of diethyl ether. The precipitated polymer was filtered and again purified by re-precipitation, to give 14.34 g of the desired polymer (yield: 85%).

GPC analysis: Weight average molecular weight (Mw) 28500 (as polystyrene), Dispersion (Mw/Mn) 2.99.

Synthetic Example 7

Synthesis of polymer having solely the repeating constitutional unit in which $R^7$ to $R^{11}$ are hydrogen atoms in the general formula (3) (the following)

[Formula 38]

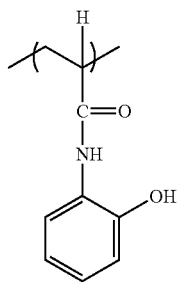

In 30 mL of tetrahydrofuran was dissolved 10 g of the acrylamide derivative obtained in the Synthetic Example 1. To the solution was added 0.201 g of 2,2'-azobis(isobutyronitrile), and the mixture was heated at reflux under an argon atmosphere for 4 hours. After cooled, it was re-precipitated in 300 mL of diethyl ether. The precipitated polymer was collected by filtration and again purified by re-precipitation, to give 9.4 g of the desired polymer (yield: 94%).

GPC analysis: Weight average molecular weight (Mw) of 4900 (converted to polystyrene), Dispersion (Mw/Mn) of 2.33

Example 11

A chemically amplified positive photosensitive resin composition was prepared, in such a may that: (a) 6 g of the polymer obtained in the Example 4, (b) 0.144 g of a photoacid generator (N-(p-toluenesulfonyloxy)naphthalimide, Midori Kagaku Co. Ltd., trade name: NAI-101), (c) 1.2 g of a dissolution inhibitor (the compound obtained in the Synthetic Example 2), and (d) 11.75 g of γ-butyrolactone were mixed and the mixture was filtrated through a 0.45 μm Teflon® filter.

On a 5-inch silicon substrate was spin-coated the above chemically amplified photosensitive resin composition, which was then dried in an oven at 100° C. for 20 minutes, to form a thin film with a thickness of 10 μm. Then, the film of the photosensitive resin composition was patterned by exposure with ultraviolet rays (wavelength=350 to 450 nm) via a photomask. After the exposure, it was baked in an oven at 100° C. for 10 minutes and then developed by immersing it in a 2.38% aqueous solution of tetramethylammonium hydroxide (TMAH) at room temperature for 3 minutes, and then rinsed with pure water for 2 minutes. As a result, a positive pattern was obtained, in which only the exposed area of the photosensitive resin film had been removed by dissolution in a developing solution. SEM observation of the pattern obtained indicated that resolution to a 10 μm through-hole pattern was obtained at a sensitivity of at 700 mJ/cm².

Then, the whole surface of the patterned wafer was exposed to ultraviolet rays (wavelength=350 to 450 nm) at a dose of 1000 mJ/cm² and then baked under a nitrogen atmosphere in an oven at 110° C. for 30 minutes and then at 220° C. for 1 hour, for forming a benzoxazole ring to obtain the final pattern having a thickness of 7.7 μm and exhibiting excellent properties such as heat resistance. SEM observation of the pattern formed did not indicate any crack and any delamination in the pattern.

Examples 12 to 17

Chemically amplified photosensitive resin compositions were prepared in the same manner as in the Example 11 except that the polymers obtained in the Examples 5 to 10 were used in place of the polymer obtained in the Example 4. The photosensitive resin compositions were spin-coated and patterned by exposure to form a positive pattern. Table 4 shows the evaluation results for their sensitivity and resolution in a through-hole pattern.

The obtained pattern was baked under a nitrogen atmosphere in an oven at 110° C. for 30 minutes and then at 220° C. for 1 hour, for forming a benzoxazole ring to obtain the final pattern exhibiting excellent properties such as heat resistance. SEM observation of the pattern formed did not indicate any crack and any delamination in the pattern.

Example 18

A chemically amplified photosensitive resin composition was prepared in the same manner as in the Example 11 except that the resin obtained in the Synthetic Example 6 was used in place of the polymer obtained in the Example 4 and the amount of the dissolution inhibitor to be added was changed to 1.8 g from 1.2 g. The photosensitive resin composition was spin-coated and patterned by exposure to form a positive pattern. Table 4 shows the evaluation results for their sensitivity and resolution in a through-hole pattern.

The obtained pattern was baked under a nitrogen atmosphere in an oven at 110° C. for 30 minutes and then at 220° C. for 1 hour, for forming a benzoxazole ring to obtain the final pattern exhibiting excellent properties such as heat resistance. SEM observation of the pattern formed did not indicate any crack and any delamination in the pattern.

Example 19

A chemically amplified photosensitive resin composition was prepared in the same manner as in the Example 11 except that the resin obtained in the Synthetic Example 7 was used in place of the polymer obtained in the Example 4 and the amount of the dissolution inhibitor to be added was changed to 2.4 g from 1.2 g. The photosensitive resin composition was spin-coated and patterned by exposure to form a positive pattern. Table 4 shows the evaluation results for their sensitivity and resolution in a through-hole pattern.

The obtained pattern was baked under a nitrogen atmosphere in an oven at 110° C. for 30 minutes and then at 220° C. for 1 hour, for forming a benzoxazole ring to obtain the final pattern exhibiting excellent properties such as heat resistance. SEM observation of the pattern formed did not indicate any crack and any delamination in the pattern.

TABLE 4

| | Chemically amplified photosensitive resin composition | Patterning | | Final pattern | |
|---|---|---|---|---|---|
| | | Resolution | Sensitivity | | |
| | Used polymer | (μm) | (mJ/cm³) | Crack | Delamination |
| Example 11 | Produced in Example 4 | 10 | 700 | No | No |
| Example 12 | Produced in Example 5 | 10 | 700 | No | No |
| Example 13 | Produced in Example 6 | 10 | 600 | No | No |
| Example 14 | Produced in Example 7 | 10 | 600 | No | No |
| Example 15 | Produced in Example 8 | 10 | 600 | No | No |
| Example 16 | Produced in Example 9 | 8 | 700 | No | No |
| Example 17 | Produced in Example 10 | 10 | 700 | No | No |
| Example 18 | Produced in Synthetic Example 6 | 12 | 600 | No | No |
| Example 19 | Produced in Synthetic Example 7 | 12 | 600 | No | No |

Example 20

A chemically amplified positive photosensitive resin composition was prepared in such a may that: (a) 7 g of the polymer obtained in the Example 4, (b) 0.168 g of a photoacid generator (N-(p-toluenesulfonyloxy)naphthalimide, Midori Kagaku Co. Ltd., trade name: NAI-101), (c) 1.4 g of a dissolution inhibitor (the compound obtained in the Synthetic Example 2), (d) 0.21 g of an adhesion improver (the compound obtained in the Synthetic Example 4) and (e) 11.6 g of γ-butyrolactone were mixed and the mixture was filtrated through a 0.45 μm Teflon® filter.

On a 5-inch silicon substrate on which Cu was film-formed was spin-coated the above chemically amplified photosensitive resin composition, which was then baked in an oven at 100° C. for 20 minutes, to form a thin film with a thickness of 11 μm. Then, the film of the photosensitive resin composition was patterned by exposure with ultraviolet rays (wavelength=350 to 450 nm) via a photomask. After the exposure, it was baked in an oven at 90° C. for 10 minutes and then developed by immersing it in a 2.38% aqueous solution of TMAH at room temperature for 4 minutes, and subsequently rinsed with pure water for 2 minutes. As a result, a positive pattern was formed, in which only the exposed area of the photosensitive resin film had been removed by dissolution in a developing solution. SEM observation of the pattern obtained indicated that resolution to a 10 μm through-hole pattern was obtained at a sensitivity of 700 mJ/cm².

Then, the whole surface of the patterned wafer was exposed to ultraviolet rays (wavelength=350 to 450 nm) at a dose of 1000 mJ/cm² and then baked under a nitrogen atmosphere in an oven at 95° C. for 30 minutes and then at 220° C. for 1 hour, for forming a benzoxazole ring to obtain the final pattern with a thickness of 8.8 μm, exhibiting excellent properties such as heat resistance. SEM observation of the pattern formed did not indicate any crack and any delamination in the pattern.

Example 21

A chemically amplified positive photosensitive resin composition was prepared in such a way that (a) 20 g of the polymer obtained in the Example 9, (b) 0.48 g of a photoacid generator (N-(p-toluenesulfonyloxy)naphthalimide, Midori Kagaku Co. Ltd., trade name: NAI-101), (c) 4 g of a dissolution inhibitor (the compound obtained in the Synthetic Example 3), (d) 0.6 g of an adhesion improver (the compound obtained in the Synthetic Example 5) and (e) 33.14 g of γ-butyrolactone were mixed and the mixture was filtrated through a 0.45 μm Teflon® filter.

On a 5-inch silicon substrate on which a film of Cu was formed was spin-coated the above chemically amplified photosensitive resin composition, which was then baked in an oven at 100° C. for 20 minutes, to form a thin film with a thickness of 11 μm. Then, the film of the photosensitive resin composition was patterned by exposure with ultraviolet rays (wavelength=350 to 450 nm) via a photomask. After the exposure, it was baked in an oven at 90° C. for 10 minutes and then developed by immersing it in a 2.38% aqueous solution of TMAH at room temperature for 4 minutes, and then rinsed with pure water for 2 minutes. As a result, a positive pattern was formed, in which only the exposed area of the photosensitive resin film had been removed by dissolution in a developing solution. SEM observation of the pattern obtained indicated that resolution to a 8 μm through-hole pattern was obtained at a sensitivity of 700 mJ/cm².

Then, the whole surface of the patterned wafer was exposed to ultraviolet rays (wavelength=350 to 450 nm) at a dose of 1000 mJ/cm² and then baked under a nitrogen atmosphere in an oven at 95° C. for 1 hour and then at 250° C. for 1 hour, for forming a benzoxazole ring to obtain the final pattern with a thickness of 8.3 μm, exhibiting excellent properties such as heat resistance. SEM observation of the pattern formed did not indicate any crack and any delamination in the pattern.

INDUSTRIAL APPLICABILITY

As is apparent from the above description, the chemically amplified photosensitive resin composition which can be developed with the aqueous alkaline solution and has excellent resolution is obtained by using the polymer prepared by polymerizing the monomer composition containing the (meth)acrylamide derivative of the present invention in the chemically amplified photosensitive resin composition. The chemically amplified photosensitive resin composition can be used for the interlayer insulating film and surface protection film or the like of the semiconductor device.

The invention claimed is:

1. A (meth)acrylamide derivative represented by the following general formula (1):

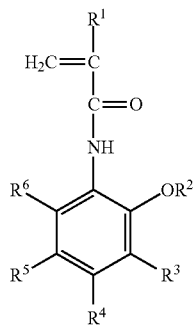

wherein,

R$^1$ represents a hydrogen atom or a methyl group;

R$^2$ represents an acid-decomposable group selected from the group consisting of 1-ethoxyethyl, 1-butoxyethyl, 1-propoxyethyl, methoxymethyl and ethoxymethyl groups; and R$^3$ to R$^6$ independently represent a hydrogen atom, a halogen atom or an alkyl group having 1 to 4 carbon atoms.

2. A polymer comprising at least one repeating constitutional unit represented by the following general formula (2):

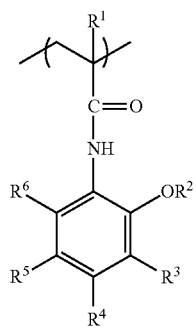

wherein,

R$^1$ represents a hydrogen atom or a methyl group; R$^2$ represents an acid-decomposable group selected from the group consisting of 1-ethoxyethyl, 1-butoxyethyl, 1-propoxyethyl, methoxymethyl and ethoxymethyl groups; and R$^3$ to R$^6$ independently represent a hydrogen atom, a halogen atom or an alkyl group having 1 to 4 carbon atoms.

3. The polymer according to claim 2, prepared by polymerizing a (meth)acrylamide derivative represented by the following general formula (1) with a vinyl monomer copolymerizable with the (meth)acrylamide derivative

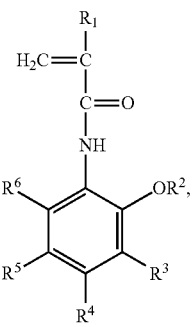

wherein,

R$^1$ represents a hydrogen atom or a methyl group;

R$^2$ represents an acid-decomposable group selected from the group consisting of 1-ethoxyethyl, 1-butoxyethyl, 1-propoxyethyl, methoxymethy and ethoxymethyl groups; and R$^3$ to R$^6$ independently represent a hydrogen atom, a halogen atom or an alkyl group having 1 to 4 carbon atoms.

4. The polymer according to claim 2, further comprising a constitutional unit represented by the following general formula (3) and/or a constitutional unit represented by the following general formula (4):

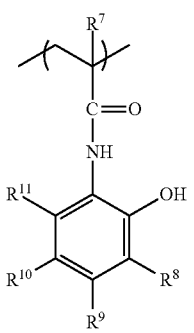

wherein,

R$^7$ represents a hydrogen atom or a methyl group; and

R$^8$ to R$^{11}$ independently represent a hydrogen atom, a halogen atom or an alkyl group having 1 to 4 carbon atoms;

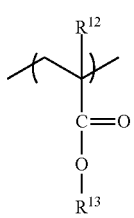

wherein,

R$^{12}$ represents a hydrogen atom or a methyl group; and

R$^{13}$ represents an organic group having a lactone structure.

5. The polymer according to claim 2, having a weight average molecular weight of 2,000 to 200,000.

6. A chemically amplified photosensitive resin composition, comprising at least a polymer containing at least one repeating constitutional unit represented by the general formula (2); and a photoacid generator,

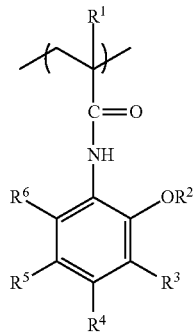

wherein,
- $R^1$ represents a hydrogen atom or a methyl group;
- $R^2$ represents an acid-decomposable group which is selected from the group consisting of 1-ethoxyethyl, 1-butoxyethyl, 1-propoxyethyl, methoxymethy and ethoxymethyl groups.

7. The chemically amplified photosensitive resin composition according to claim 6, further comprising a dissolution inhibitor and/or an adhesion improver.

8. The chemically amplified photosensitive resin composition according to claim 7, wherein the dissolution inhibitor is a compound represented by the following general formula (5) or the following general formula (6):

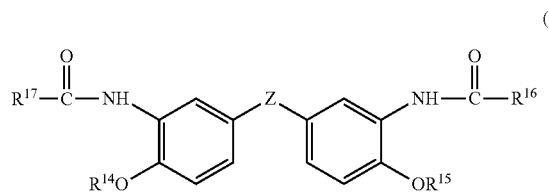

wherein,
- $R^{14}$ and $R^{15}$ represent an acid-decomposable group;
- $R^{16}$ and $R^{17}$ are a linear, branched or cyclic alkyl group or an aromatic hydrocarbon group having 1 to 10 carbon atoms; and
- Z represents a direct bond, $-C(CF_3)_2-$, $-SO_2-$, $-CO-$, $-O-$, or a divalent hydrocarbon group;

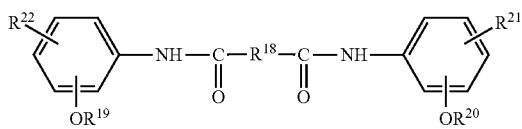

wherein,
- $R^{10}$ represents a divalent hydrocarbon group;
- $R^{10}$ and $R^{20}$ represent an acid-decomposable group; and
- $R^{21}$ and $R^{22}$ represent a hydrogen atom, a halogen atom, or an alkyl group having 1 to 4 carbon atoms.

9. A patterning method comprising:
applying the chemically amplified photosensitive resin composition according to claim 8 on a processed substrate;
pre-baking;
exposing;
after-exposure baking;
developing; and
post-baking.

10. The chemically amplified photosensitive resin composition according to claim 7, wherein the adhesion improver is an organosilicon compound.

11. The chemically amplified photosensitive resin composition according to claim 10, wherein the organosilicon compound is a compound represented by the following general formula (7):

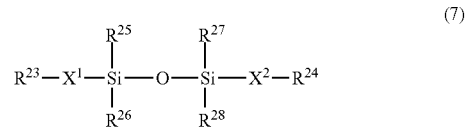

wherein,
- $R^{23}$ to $R^{28}$ represent a monovalent organic group; and
- $X^1$ and $X^2$ represent a divalent organic group.

12. A patterning method comprising:
applying the chemically amplified photosensitive resin composition according to claim 10 on a processed substrate;
pre-baking;
exposing;
after-exposure baking;
developing; and
post-baking.

13. A patterning method comprising:
applying the chemically amplified photosensitive resin composition according to claim 7 on a processed substrate;
pre-baking;
exposing;
after-exposure baking;
developing; and
post-baking.

14. The chemically amplified photosensitive resin composition according to claim 6, wherein the polymer containing the repeating constitutional unit represented by the general formula (2) is prepared by polymerizing a (meth)acrylamide derivative represented by the following general formula (1) with a vinyl monomer copolymerizable with the (meth) acrylamide derivative

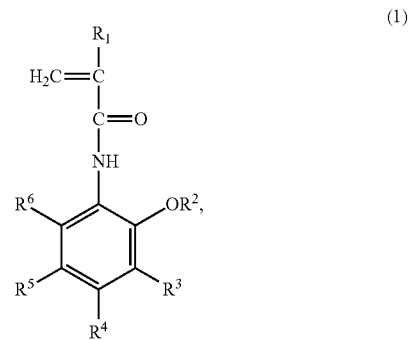

wherein, $R^1$ represents a hydrogen atom or a methyl group;

$R^2$ represents an acid-decomposable group selected from the group consisting of 1-ethoxyethyl, 1-butoxyethyl, 1-propoxyethyl, methoxymethy and ethoxymethyl groups; and $R^3$ to $R^6$ independently represent a hydrogen atom, a halogen atom or an alkyl group having 1 to 4 carbon atoms.

15. The chemically amplified photosensitive resin composition according to claim 6, wherein the polymer containing the repeating constitutional unit represented by the general formula (2) further comprises a constitutional unit represented by the general formula (3) and/or a constitutional unit represented by the following general formula (4)

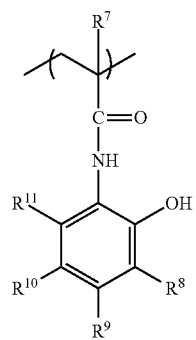

(3)

wherein $R^7$ represents a hydrogen atom or a methyl group; and $R^8$ to $R^{11}$ independently represent a hydrogen atom, a halogen atom or an alkyl group having 1 to 4 carbon atoms;

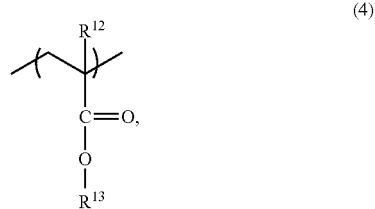

(4)

wherein, $R^{12}$ represents a hydrogen atom or a methyl group; and $R^{13}$ represents an organic group having a lactone structure.

16. The chemically amplified photosensitive resin composition according to claim 6, wherein the polymer containing the repeating constitutional unit represented by the general formula (2) has a weight average molecular weight of 2,000 to 200,000.

17. A patterning method comprising:
applying the chemically amplified photosensitive resin composition according to claim 6 on a processed substrate;
pre-baking;
exposing;
after-exposure baking;
developing; and
post-baking.

18. The patterning method according to claim 17, further comprising post-exposing between the developing and the post-baking.

* * * * *